United States Patent [19]

Lehner et al.

[11] Patent Number: 5,612,031

[45] Date of Patent: *Mar. 18, 1997

[54] ANTIBODIES AGAINST STREPTOCOCCUS

[75] Inventors: Thomas Lehner; Roberta Smith, both of London, England

[73] Assignee: Council of Governors of the United Medical School and Dental Schools of Guy's and St. Thomas's Hospital, London, England

[*] Notice: The term of this patent shall not extend beyond the expiration date of Pat. No. 5,518,721.

[21] Appl. No.: 481,732

[22] Filed: Jun. 7, 1995

Related U.S. Application Data

[63] Continuation of Ser. No. 301,481, Sep. 7, 1994, Pat. No. 5,518,721, which is a continuation of Ser. No. 80,693, Jun. 22, 1993, abandoned, which is a continuation of Ser. No. 970,655, Nov. 2, 1992, abandoned, which is a continuation of Ser. No. 806,814, Dec. 6, 1991, abandoned, which is a continuation of Ser. No. 399,515, filed as PCT/GB88/00135, Feb. 26, 1988, abandoned.

[30] Foreign Application Priority Data

Feb. 27, 1987 [GB] United Kingdom ............... 8704648
Feb. 26, 1988 [WO] WIPO ................ PCT/GB88/00135

[51] Int. Cl.$^6$ ................. A61K 39/40; A61K 39/395; C07K 16/28; C12P 21/08
[52] U.S. Cl. ................ 424/150.1; 424/156.1; 424/163.1; 424/164.1; 424/165.1; 530/388.2; 530/388.4; 435/172.1; 435/70.21
[58] Field of Search ................ 530/388.2, 388.4; 424/150.1, 156.1, 163.1, 164.1, 165.1; 435/70.21, 172.1, 240.27

*Primary Examiner*—Susan A. Loring
*Attorney, Agent, or Firm*—Morrison & Foerster LLP

[57] ABSTRACT

Antibodies which bind the surface antigen I/II of *Streptococcus sobrinus* serotype d and cross react with the surface antigen I/II of *Streptococcus mutans* serotypes c, e, f and g and method to combat dental caries by applying the antibodies which bind the surface antigen I/II of *Streptococcus sobrinus* serotype d and cross react with the surface antigen I/II of *Streptococcus mutans* serotypes c, e, f and g.

2 Claims, No Drawings

ANTIBODIES AGAINST STREPTOCOCCUS

This application is a continuation of application Ser. No. 08/301,481, filed 7 Sep. 1994, now U.S. Pat. No. 5,518,721, which is a continuation of Ser. No. 08/080,693, filed 22 Jun. 1993, now abandoned, which is a continuation of Ser. No. 07/970,655, filed 2 Nov. 1992, now abandoned, which is a continuation of Ser. No. 07/806,814, filed 6 Dec. 1991, now abandoned, which is a continuation of Ser. No. 07/399,515, filed 27 Oct. 1989, now abandoned, which is a 371 of PCT/GB88/00135, filed 26 Feb. 1988.

FIELD OF THE INVENTION

This invention relates to antibodies useful to combat dental caries.

BACKGROUND TO THE INVENTION

*Streptococcus mutans* has been recognised for many years as the major organism responsible for the development of dental caries in mammals. Various vaccines have been proposed in the past based on various antigenic fragments of *S. mutans*. One such vaccine is described in British Patent No. 2,060,647 based upon the antigen known as I or I/II. Antigen I has a molecular weight, as determined by sodium dodecyl sulphate polyacrylamide gel electrophoresis (SDS-PAGE) of 146–155 Kd. Antigen I/II is believed to be a conjugate of antigen I and antigen II, this I/II antigen having a molecular weight determined by SDS-PAGE of 175–195 Kd. Published European Patent Application No. EP-A-0 116 472 describes antigen X which is a much smaller molecule having a molecular weight, determined by SDS-PAGE of about 3.5–4.5 Kd but which appears to include the same antigenic determinants included within antigens I and I/II.

Antibodies against antigens I, I/II and X are known. The above-mentioned British Patent describes the raising of antibodies against antigens I and I/II by conventional procedures in experimental animals, for example rhesus monkeys, rabbits and mice. These antibodies are proposed primarily for the purification of the antigen by affinity chromatography but the Patent Specification mentions the possibility of using such antibodies for passive immunisation by conventional means. Conventional passive immunisation involves parenteral administration of the antibodies but while such techniques are theoretically available, as a practical matter, passive immunisation has never been regarded as clinically attractive and indeed, the British Patent refers to the preferred use of the antigenic materials for direct immunisation.

All antibodies that have been raised against *S. mutans* serotype c or against the streptococcal antigen serotype c ($SA_c$) exhibit a certain degree of cross-reactivity. It is well known that such antibodies are also cross-reactive with antigenic material originating from serotypes e and f of *S. mutans*. In clinical practice, it is found that serotypes c, e and f amount to about 90% of the bacterial *S. mutans* population so that the prophylactic or therapeutic use of antibodies raised against serotype c are of considerable practical value but fail to be effective in relation to the residual approximately 10% of the bacterial population. In some series serotype d is found in addition to serotype c in up to 50% of children examined.

This residual 10% is comprised predominantly of a serotype d that until very recently has been regarded merely as another serotype of *S. mutans*. However recently, this particular serotype has been reclassified as *S. sobrinus* and, in the description of this invention, we will use the nomenclature *S. sobrinus* serotype d rather than *S. mutans* serotype d.

We have now found that if antibodies are raised against *S. sobrinus* serotype d, that many of the resulting antibodies are cross-reactive not only with *S. sobrinus* serotype d and also *S. sobrinus* (*S. mutans*) serotype g (and serotype a) but surprisingly, that such antibodies are also cross-reactive with serotypes c, e and f of *S. mutans*. Since somewhere of the order of 98% of all serotypes of *S. mutans/S. sobrinus* found in the oral cavities are of serotypes a, c, d, e, f and g, our discovery has enabled us to produce, for the first time, antibodies having the potential for prophylactic and/or therapeutic use in relation to substantially 100% of oral bacteria of *S. mutans/S. sobrinus* type that are responsible for dental caries.

Accordingly, the present invention provides antibodies against a common determinant of *S. sobrinus* serotypes d and *S. mutans* serotype c.

The antibodies of the present invention extend not only to whole antibodies but also to antibody fragments containing the necessary binding sites to enable them to recognise and bind with the streptococcal antigen and the antibodies or fragments thereof may be prepared in polyclonal or monoclonal form.

The antibodies of the invention can be raised using *S. sobrinus* serotype d or streptococcal antigen derived therefrom as the immunogen. Normally, the immunogen will comprise the naturally-occurring streptococcal antigen but, as is the case with the use of streptococcal antigen from serotype c of *S. mutans*, use can also be made of antigenic fragments of serotype d, provided that those antigenic fragments contain the necessary antigenic determinants characteristic of serotype d.

For the production of polyclonal antibodies, conventional methods may be used involving the immunisation of animals with the serotype d immunogen followed by recovery of the antibodies from the blood of the immunised animals. Conventional antibody recovery methods can be used and conventional antibody purification methods can be used, e.g. affinity chromatography using purified immunogen or fragments thereof.

Where monoclonal antibodies are to be raised, the immunogen derived from serotype d can be used conventionally to immunise mice or other mammals and the spleen of the immunised mammal hybridised with myeloma cells to produce a population of hybridoma cells. Alternatively, immunogen derived from serotype d can be used for in vitro stimulation of B-lymphocytes and the stimulated B-lymphocytes then hybridised with myeloma cells by methods known per se to provide a population of hybridomas. The resulting population of hybridomas may then be screened to select those secreting monoclonal antibody that is cross-reactive by *S. sobrinus* serotype d and *S. mutans* serotype c. When polyclonal antibodies are produced, they may also be screened to select those showing the serotype d/c cross-reactivity. The antibodies, however produced, can be purified if necessary by affinity chromatography techniques or by staphylococcal protein A to separate IgG class of antibodies or by using serotype d antigen.

Where antibody fragments are required, the polyclonal or monoclonal antibody produced by the methods described above can be fragmented by digestion with papain or pepsin by conventional methods.

DETAILED DESCRIPTION OF THE INVENTION

While the present invention is directed primarily to humans, the problem of dental caries is not confined to humans but arises in other mammals including non-human primates, domestic and farm animals and particularly in those cases where the non-human mammal eats a substantial proportion of food including sugars.

The monoclonal antibodies used in this invention may be applied to the tooth in the mouth of the mammal by any convenient method. Numerous methods are now available for the treatment of teeth with various materials for various purposes. If the treatment is to be carried out by a Dental Surgeon, then the monoclonal antibody is conveniently applied by painting the surface of the tooth. If the monoclonal antibodies are to be self-applied, then the monoclonal antibodies may be included in a toothpaste, mouthwash, chewing gum, lozenge or gel. As will be described in more detail below, the duration of protection afforded by the method of the present invention is surprisingly long but the frequency of the topical application is primarily one for the users personal convenience. Methods of self-application from toothpastes etc., can result in applications being repeated perhaps daily while the use of lozenges can result in more frequent application of the antibody. Chewing gums and gels may be regarded, for this purpose, as providing a certain amount of sustained release of the antibody over a period of half-an-hour or more and indeed, if sustained release of the antibody is required, then appropriate formulations can be used that will result in slow release of antibody into the mouth from the formulation as a result of the temperature or saliva conditions etc., found in the mouth. In certain instances, it may be desirable to provide a more formal prolonged contact of the antibody with the tooth surface and in such cases, appropriate dental trays can be used that will cover the tooth after it has been coated with antibody and prevent the antibody from being removed, e.g. by saliva, for a predetermined period.

It is important that the antibody be brought into contact with the surface of the tooth and ideally should be applied to all of the smooth and occlusal surfaces of the tooth. It is not detrimental for the antibody to contact the gum but the protection afforded by the present invention does appear to result primarily if not exclusively from the contact of the antibody with the surface of the tooth itself.

Topical administration of the antibodies is the most practical course for self-administration.

The exact amount of antibody that is applied does not appear to be critical since, in a method of this type, repeated self-application of antibody is not difficult and indeed, particularly after initial treatment by a Dental Surgeon, maintenance or top-up treatment can be carried out by the user at whatever frequency is desirable. By way of guidance, it can be indicated that somewhere of the order of 10 to 100 micrograms of antibody can be applied to each tooth on each occasion that antibody is applied but amounts of antibody outside this range can certainly be applied without causing detriment to the subject. The use of insufficient quantities of antibody simply means that the level of protection is not as great as would otherwise be obtainable while the use of excessive amounts of antibody does not improve the protection and simply results in unnecessary use of antibody.

The exact formulation for the antibody is not a matter of critical importance but depends entirely upon the method of application to be adopted and the convenience of the user. In all cases, it is important to formulate the antibody in an environment of appropriate pH and which is free from other deleterious materials which might bring about protein degradation and the formulation should, of course, also be free from microbial impurity that would be deleterious in the subject's mouth. For example, for use in the dental surgery, the antibody could be formulated as a simple aqueous dispersion containing somewhere in the region of 0.1 to 10 milligrams of antibody per 100 microliters of liquid and a liquid of such concentration could be applied to the tooth at the rate of about 1 to 10 microliters of dispersion per tooth. Where the antibody is to be formulated for self-administration, then the concentration can be selected bearing in mind the above guidelines, the quantities of the formulation that are normally taken on each occasion of self-administration and the fact that over administration of antibody will not be deleterious.

The following Examples are given to illustrate the invention.

Materials and Methods

Organisms

*S. mutans* serotypes and strains were obtained from a number of laboratories as described previously (Smith, Lehner, Beverley, 1984). Samples of serotype d strains (FRID and Lee) were isolated in our laboratories. Strain AHT, originally described as serotype a however, has been apparently reclassified to serotype g; hence no results are presented for serotype a.

Streptococcal antigens (SA)

SA from serotype d (strains FRID and OMZ 176) were prepared from culture supernatants by combination of ammonium sulphate precipitation, ion exchange chromatography and gel filtration, as described previously (Russell et al 1980). Antigen dI/II, equivalent to cI/II of serotype c (185 Kd) was characterised using cross-reactive polyclonal rabbit antisera to SA cI/II.

Production of monoclonal antibodies (McAb)

McAb to SA dI/II were prepared by a method similar to that of Smith et al 1984 following the procedure of Fazekas de St. Groth and Scheidegger (1980). Briefly Balb c mice were immunised with 10 ug SA dI/II (strain FRID) intraperitoneally in Freund's complete adjuvant, followed two weeks later by 10 ug SA dI/II in Freund's incomplete adjuvant. The third and final injection, again two weeks later was given intravenously in saline and the mouse was bled and sacrificed four days later and the spleen was removed. Immune mouse spleen cells were fused at a ratio of 1:1 with the mouse myeloma line P3-NS1/1-Ag4-1 (NS1), in the presence of 50% (wt/vol) polyethylene glycol (PEG 4000 d; Sigma chemical Co.) in RPMl 1640 (Gibco Laboratories). The PEG was neutralised with 10N sodium hydroxide prior to use.

After fusion the cells were plated out at $2 \times 10^5$ total viable cells per well, in 24 well cluster plates (Costar plastics, Cambridge, Mass.). Feeder cells from peritoneal lavage of BALB/c mice were added at $3 \times 10^4$ cell/well. Throughout cloning, RPMl 1640, supplemented with 10% foetal calf serum, glutamine (2 mM), pyruvate (1 mM) and antibiotics was used. For the first two weeks after fusion the medium was further supplemented with hypoxanthine, aminopterin and thymidine to eliminate unfused NS1 cells. By the third week only hypoxanthine and thymidine were added. After 10 to 14 days the supernatants of wells showing growth were assayed for specific antibodies to the purified SA and to heart homogenate (Bergmeier and Lehner 1983) in a micro-solid-phase radioassay, as described previously (Smith et al 1984). Cultures giving binding greater than 3 times the background were cloned, at least twice by the method of limiting dilution to 0.3 cells per well and dispensed in the presence of $5 \times 10^3$ feeder cells and $5 \times 10^4$ normal spleen cells, into 96-well plates, with flat bottom wells (Costar). Cloned cells were expanded and then injected into pristane primed mice for ascites. Culture supernatants were stored at 4° C. with 0.1% sodium azide and ascites at −20° C. The cells were frozen in the presence of 10% dimethyl sulphoxide, 50% foetal calf serum in RPMl 1640 and stored in liquid nitrogen.

Characterisation of the McAb

The isotype of the McAb was determined by double diffusion precipitation in 1% agarose, using culture supernatants of the McAb and reactions with commercial antisera (Nordic) for IgG1, IgG2a and (Eivai Bios) for IgM. The specificity of the McAb was tested by titrating each McAb against purified SA dI/II, derived from S. sobrinus serotype d (FRID, OMZ 176) or S. mutans serotype c (Guy's strain) as well as against whole cells of the other serotypes and S. sanguis (OMZ 9), by the radioassay (Smith et al 1984).

Inhibition studies of McAb with purified SA for antigen specificity

Ascitic fluids of the McAb were diluted with PBS containing 0.5% bovine serum albumin and 0.05% Tween 20, to give approximately 50% binding to SA dI/II (FRID) by micro-solid-phase radioassay. 200 µl samples of dilute McAb were incubated with 5 µg of SA dI/II (FRID), or saline overnight at 4° C. The samples were then examined by the radioassay for antibody binding to SA dI/II.

Results

Characterisation of McAb

TABLE 1

| Code | Strep. mutans antigen specificity | Antibody class | Serotype specificity |
| --- | --- | --- | --- |
| Guy's 1 | serotype c I/III | IgG2a | c, e, f |
| Guy's 11 | serotype c I/II & d I/II | IgG2b | a, c, d, e, f, g |
| Guy's 12 | serotype c I/II & d I/II | IgG1 | c, d, e, f, g |
| Guy's 13 | serotype c I/II & d I/II | IgG1 | a, c, d, e, f, g | serotype h not tested

We have prepared and characterised various monoclonal antibodies (McAb) against various SA from serotype c and d (Table 1). Guy's 1 (formerly 2D4), was prepared using the antigen for which it is specific as immunogen. McAb to SA dI/II, Guy's 11, 12 and 13 were derived from a single fusion, using SA dI/II (FRID) as immunogen. The McAb belong to IgG1, IgG2a and IgM class as shown in Table 1.

Ascitic fluid of the McAb titrate to >$10^{-6}$, as measured by the radioassay against SA dI/II for Guy's 11, 12, 13 or SA cI/II for Guy's 1. Similarly, using the fluid phase radioassay against whole cells of S. mutans, the McAb which bind to SA dI/II also bind in high titres (>$10^{-6}$) to the cell surface of serotype d (OMZ 176). Guy's 1, equivalent to SA cI/II, also shows titres of >$10^{-6}$ against the whole cells of serotype c (Guy's).

SA specificity

The specificity of McAb Guy's 1 has been demonstrated Previously for SA cI/II, I, II and III by direct binding and competitive inhibition in the radioassay. Examination of the binding of Guy's 1 to SA dI/II was negative. However, Guy's 11, 12 and 13 react with SA I/II derived from both S. mutans and S. sobrinus.

Serotype specificity

Binding of McAb to the surface of different serotypes of S. mutans and S. sobrinus was examined by the fluid phase radioassay against whole cells. Guy's 1 bound to the surface of serotype c (Guy's strain) and cross-reacted with serotype f (OMZ 175). It also showed low but significant binding to serotype e, giving the classical serotype cross-reactions for S. mutans (c, e, f). Guy's 11, 12 and 13 reacted with S. mutans serotypes, c, e, f and a ( except 12) and S. sobrinus serotypes d and g. None of the McAb gave any significant binding to S. sanguis.

We have prepared McAb which are specific for S. mutans serotypes c, e and f and S. sobrinus serotypes d and g. McAb to S. mutans or S. sobrinus are of the IgG1 and IgG2a classes but S. sobrinus also elicited McAb of the IgM class. We have demonstrated the specificity of McAb for cell surface SA I/II, I, II or III by direct binding and competitive inhibition. McAb reacting to serotype cI/II do not bind to serotype dI/II but the three monoclonal antibodies raised by immunisation with S. sobrinus showed a broad reactivity with S. mutans and S. sobrinus serotypes. This suggests that Guy's 11, 12 and 13 are most likely directed against a common determinant of the mutans type of streptococci and are therefore particularly convenient reagents to be used against colonisation of S. mutans and S. sobrinus. These SA are expressed on the cell surface (Zanders and Lehner 1981, Moro and Russell 1985) and are here shown to bind strongly McAb in a fluid phase radioassay. The McAb show high titres (>$10^{-6}$), in binding both to purified SA and to the SA on the cell surface.

REFERENCES

1. Bergmeier L. A. and T. Lehner. 1983. Infect. Immun. 40:1075–1082.
2. Fazekas de St. Groth S. and D. Scheidegger. 1980. J. Immunol. Methods 35:1–21.
3. Moro I. and M. W. Russell. 1983. Infect. Immun. 41:410–413.
4. Russell, M. W., L. A. Bergmeier, E. D. Zanders and T. Lehner. 1980. Infect. Immun. 28:486–493.
5. Russell, M. W., L. A. Bergmeier, E. D. Zanders and T. Lehner. 1980. Infect. Immun. 29:999–1006.
6. Smith, R., T. Lehner and P. C. L. Beverley. 1984. Infect. Immun. 46:168–175.
7. Zanders E. D., and T. Lehner. 1981. J. Gen. Microbiol. 122:217–225.

We claim:

1. An antibody or antigen binding fragment thereof obtained by using as an immunogen the surface antigen I/II of *Streptococcus sobrinus* serotype d or a fragment of said antigen retaining epitopes characteristic of the surface antigen I/II of *S. sobrinus* serotype d, wherein said antibody or antigen binding fragment reacts with the surface antigen I/II of said serotype d, and cross-reacts with the surface antigen I/II of *Streptococcus mutans* serotypes C, e, f and g.

2. A method to combat dental caries in a mammal which comprises applying to the teeth of the mammal an effective amount of the antibody or antigen binding fragment of claim 1.

* * * * *